US009459168B2

(12) United States Patent  
Kohuth et al.

(10) Patent No.: US 9,459,168 B2
(45) Date of Patent: Oct. 4, 2016

(54) HIGH SENSITIVITY, LOAD ALLEVIATING LOAD SENSOR FOR STRUT APPLICATION

(71) Applicant: Moog Inc., East Aurora, NY (US)

(72) Inventors: Kerry Randall Kohuth, Riverton, UT (US); Derek Pedersen, South Jordan, UT (US)

(73) Assignee: Moog Inc., East Aurora, NY (US)

( * ) Notice: Subject to any disclaimer, the term of this patent is extended or adjusted under 35 U.S.C. 154(b) by 200 days.

(21) Appl. No.: 14/222,061

(22) Filed: Mar. 21, 2014

(65) Prior Publication Data

US 2015/0346043 A1    Dec. 3, 2015

Related U.S. Application Data

(60) Provisional application No. 61/804,559, filed on Mar. 22, 2013.

(51) Int. Cl.

| G01L 5/22 | (2006.01) |
|---|---|
| G01N 3/08 | (2006.01) |
| B64C 13/00 | (2006.01) |
| B64C 9/16 | (2006.01) |
| B64C 9/20 | (2006.01) |
| B64C 13/34 | (2006.01) |
| G01L 5/00 | (2006.01) |
| B64D 45/00 | (2006.01) |

(52) U.S. Cl.
CPC . *G01L 5/22* (2013.01); *B64C 9/16* (2013.01); *B64C 9/20* (2013.01); *B64C 13/00* (2013.01); *B64C 13/34* (2013.01); *G01L 5/0028* (2013.01); *G01N 3/08* (2013.01); *B64D 2045/0085* (2013.01)

(58) Field of Classification Search
CPC ... B60G 2400/60; B64C 13/00; B64C 13/34; B64C 9/16; B64C 9/20; G01L 5/0028
USPC .......................................................... 73/818
See application file for complete search history.

(56) References Cited

U.S. PATENT DOCUMENTS

| 4,103,532 | A | * | 8/1978 | Buzzi | G01M 17/04 73/11.08 |
|---|---|---|---|---|---|
| 4,800,751 | A | * | 1/1989 | Kobayashi | B60G 15/068 73/117.03 |
| 5,086,649 | A | | 2/1992 | Yamaoka | |
| 5,127,637 | A | * | 7/1992 | Castel | B60G 17/019 177/141 |
| 5,152,547 | A | * | 10/1992 | Davis | B60G 17/018 188/313 |
| 5,226,635 | A | * | 7/1993 | Nakamura | B60G 13/16 267/220 |
| 6,517,060 | B1 | | 2/2003 | Kemeny | |

(Continued)

*Primary Examiner* — Freddie Kirkland, III  
(74) *Attorney, Agent, or Firm* — Hodgson Russ LLP

(57) ABSTRACT

A load-sensing strut has a main body (26) having a longitudinal loading axis (A) along which an applied load is transmitted, and a load sensing member (38) arranged to carry at least a portion of the applied load when the load is within a predetermined range, wherein the load sensing member (38) includes at least one load sensor (46) generating a load signal. The strut also has a load alleviation member (36) arranged to reduce the portion of the applied load carried by the load sensing member (38) when the applied load is outside the predetermined loading range. Consequently, the load sensors exhibit greater sensitivity to incremental changes in the applied load within the predetermined range, yet the strut provides high strength and is capable of reacting to very high loads outside of the predetermined range. The strut may be used in actuating aircraft control surfaces in a high-lift system.

13 Claims, 6 Drawing Sheets

(56) References Cited

U.S. PATENT DOCUMENTS

| | | | |
|---|---|---|---|
| 7,429,053 B2* | 9/2008 | Katagiri | B60G 7/02 180/299 |
| 8,267,383 B2* | 9/2012 | Gagliano | F16F 1/38 267/140.11 |
| 2010/0313682 A1 | 12/2010 | Morita et al. | |

* cited by examiner

HIGH SENSITIVITY, LOAD ALLEVIATING LOAD SENSOR FOR STRUT APPLICATION

CROSS-REFERENCE TO RELATED APPLICATION

This application claims priority benefit of U.S. Provisional Patent Application No. 61/804,559 filed Mar. 22, 2013, the entire disclosure of which is incorporated herein by reference.

FIELD OF THE INVENTION

The present invention relates generally to measurement of structural loading conditions to detect failures and mitigate structural damage that may result. By way of non-limiting example, the invention has specific application in the field of actuation of aircraft control surfaces in a high-lift system.

BACKGROUND OF THE INVENTION

Aircraft control surfaces, for example flaps located on the trailing edge of a fixed wing, may be driven by rotary actuators, sometimes referred to as "geared rotary actuators" or "GRAs", as part of a high-lift system of the aircraft. A drive strut may be arranged to transmit loads between an output crank of the GRA and the flap. More specifically, the drive strut may have a first end rotatably coupled to the GRA output crank and a second end rotatably coupled to the flap, wherein rotational motion of the GRA crank is transmitted to the flap to cause the flap to change position in a manner determined by a mounting linkage associated with the flap. The drive strut also acts in arresting and holding the flap in any gated or intermediate position of the flap. The GRAs in such high-lift system may be responsive to motion commands from a slat flap control computer ("SFCC").

In some aircraft flap systems, the drive strut is configured as a load sensing drive strut ("LSDS") capable of measuring loading conditions experienced by the LSDS and providing a load signal to the SFCC or to another control device indicative of loading experienced by the LSDS.

Some strut applications, including the LSDS aircraft application described above, require a very high load carrying capability for normal usage but also must sense when a structural disconnect occurs. If the drive strut becomes disconnected from either the GRA or the flap, the high-lift system will malfunction. In the event of a disconnect malfunction, it is desirable to prevent further flap movement commands from being sent to the GRA to mitigate structural damage. In the present example of an aircraft flap system, the ratio of the loading region of interest where a structural disconnect may occur to the ultimate load carrying capability of the drive strut may be a factor of 40 to 50. Furthermore, the requirement for accuracy in the loading measurement, on a full scale basis, may be 1 part in 400 (0.25%) or even tighter. This presents a challenge in the design of a LSDS.

SUMMARY OF THE INVENTION

The present invention provides a load-sensing strut having heightened sensitivity to changes in applied load in a predetermined loading range which may correspond to a loading region of interest in which a structural disconnect may occur, and further having a very high load carrying capability well beyond the region of interest. The load-sensing strut may be used, for example, in actuating aircraft control surfaces in a high-lift system.

A load-sensing strut of the present invention generally comprises a main body having a longitudinal loading axis along which an applied load is transmitted, a load sensing member arranged to carry at least a portion of the applied load when the applied load is within a predetermined loading range, and a load alleviation member arranged to reduce the portion of the applied load carried by the load sensing member when the applied load is outside the predetermined loading range. The load sensing member includes at least one load sensor generating a load signal. Because the load sensing member carries a greater portion of the applied load when the applied load is within the predetermined loading range as compared to when the applied load is outside the predetermined loading range, the load sensor or load sensors associated with the load sensing member exhibit greater sensitivity to incremental changes in the applied load when the applied load is within the predetermined loading range than when the applied load is outside the predetermined loading range.

In an embodiment of the invention, the predetermined loading range may include a tension load and a compression load. The load sensing member may include a cylindrical sleeve aligned on the loading axis, wherein a plurality of load sensors are applied to a surface of the cylindrical sleeve in angularly spaced arrangement about the loading axis. A preload member, for example a threadably adjustable nut, may be provided to apply an axially-directed preload to the load sensing member.

The load alleviation member may include an outer tube member surrounding the main body of the strut, wherein the load alleviation member is aligned on the loading axis. In a particular embodiment, the load alleviation member is situated between a collar arranged about the main body and an abutment ring arranged about the main body, the main body includes a flange opposing the collar to define an annular space between the flange and the collar, and the load alleviation member includes an internal radial step received in the annular space. The strut may further comprise an elastically deformable member arranged between the flange and the collar to maintain a gap between the flange and the internal radial step and a gap between the collar and the internal radial step when the applied load is within the predetermined loading range. When the applied load is within the predetermined loading range, the load alleviation member is not part of the loading path through the strut. However, when the applied load is outside of the predetermined loading range, at least one of the gaps closes such that the load alleviation member becomes part of the loading path through the strut.

BRIEF DESCRIPTION OF THE DRAWING VIEWS

Features and advantages of embodiments of the present disclosure will become apparent by reference to the following detailed description and drawings, in which.

DETAILED DESCRIPTION OF THE INVENTION

Figure 1:
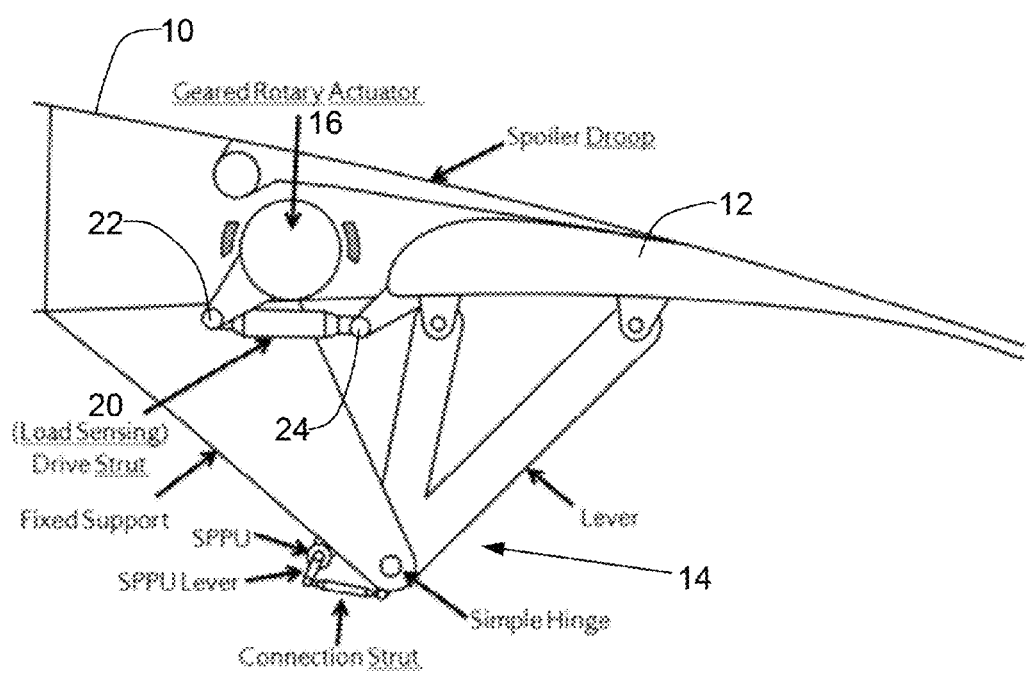
FIG. 1 is a schematic view showing an aircraft flap system incorporating a load sensing drive strut formed in accordance with an embodiment of the present invention.
Figure 2:
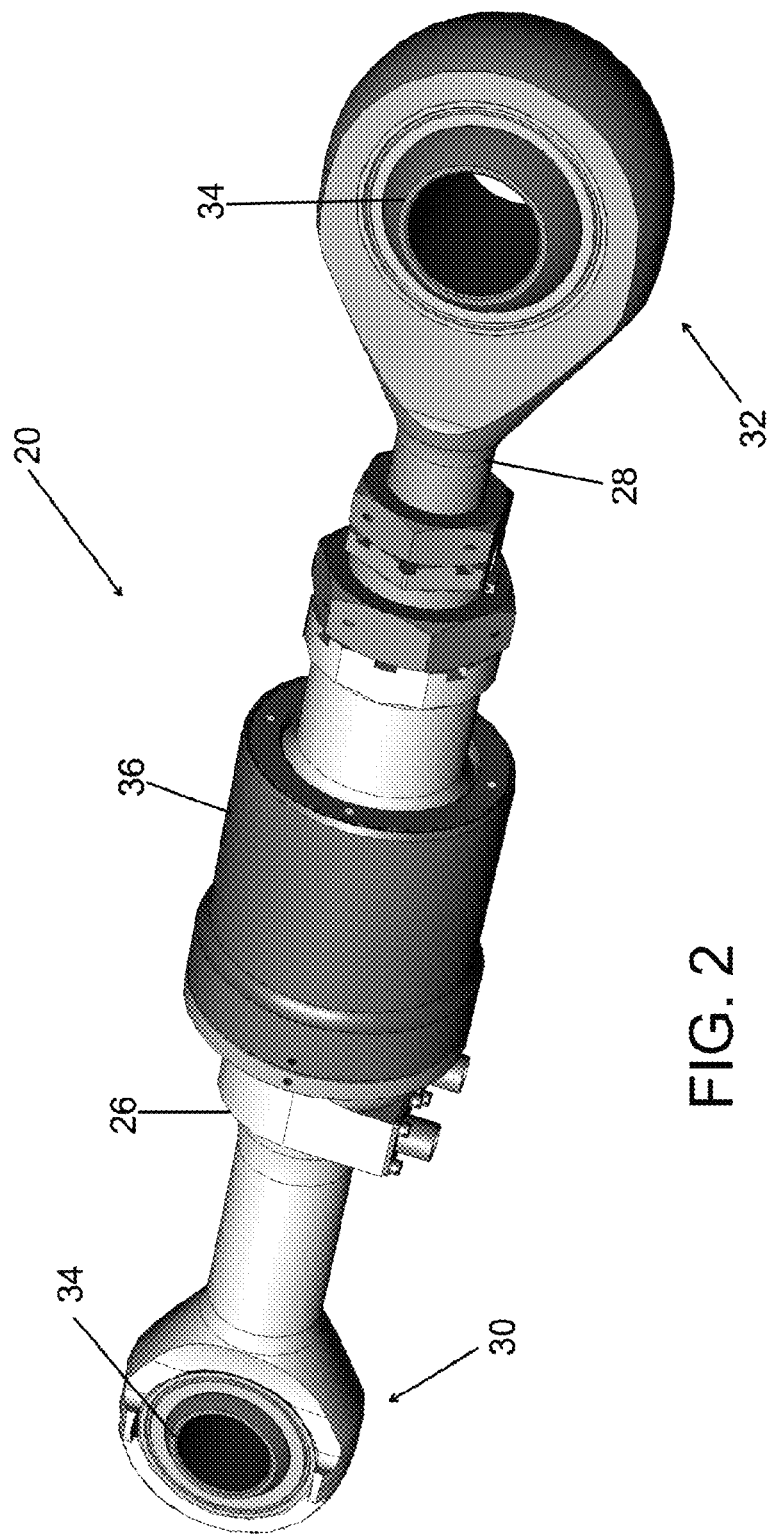
FIG. 2 is a perspective view of a load sensing drive strut formed in accordance with an embodiment of the present invention.

FIG. 1 shows an aircraft flap system as one example of an application in which a LSDS of the present invention is useful. While one example application is described herein, the present invention is not limited to this application and has utility in a wide variety of applications in which a structural member is subjected to loading.

The aircraft flap system shown in FIG. 1 includes a fixed wing 10 and a trailing edge flap 12 connected to fixed wing 10 by a mounting linkage 14 permitting adjustment of flap 12 relative to fixed wing 10 to control aerodynamic properties. A rotary actuator 16 is mounted on fixed wing 10 for driving the adjustment movements of flap 12. Rotary actuator 16 is connected to flap 12 by a LSDS 20 coupled at one end thereof to a crank member of the rotary actuator 16 by a rotary joint 22 and coupled at its opposite end to flap 12 by a rotary joint 24. As may be understood, LSDS 20 transmits loading between rotary actuator 16 and flap 12, whereby rotary actuator 16 is operable to adjust the position of flap 12 relative to fixed wing 10.

In accordance with the present invention, LSDS 20 is constructed in a manner such that when LSDS 20 is exposed to external loads, it behaves in a non-linear manner that provides higher sensitivity to loads within a specific region of interest within a larger range of loading, and provides lower sensitivity to loads outside of the region of interest. In the example of sensing drive strut disconnect in a flap system, the region of interest corresponds to relatively low load conditions.

Figure 3:
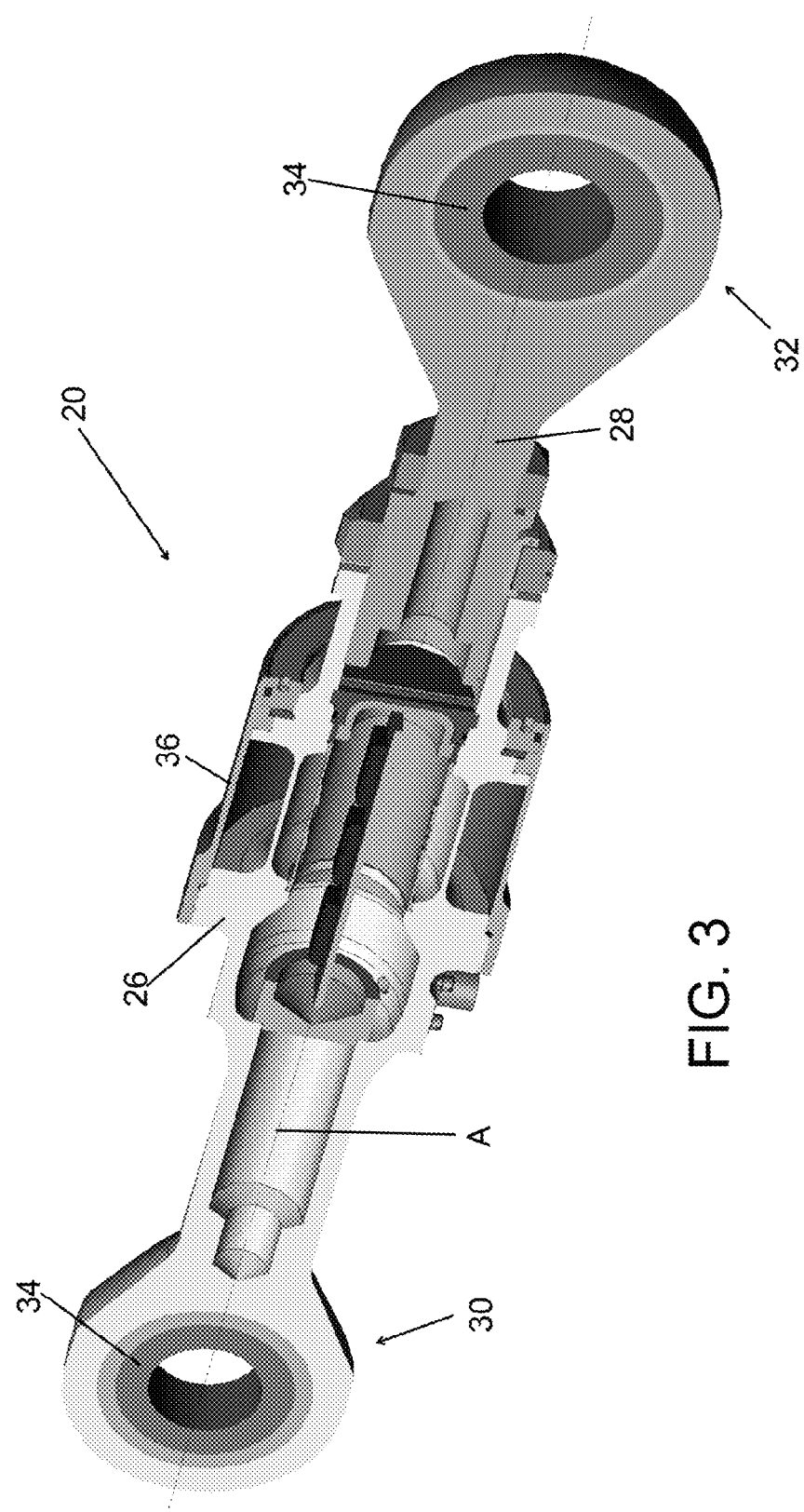
FIG. 3 is a sectioned perspective view of the load sensing drive strut shown in FIG. 2.
Figure 4:
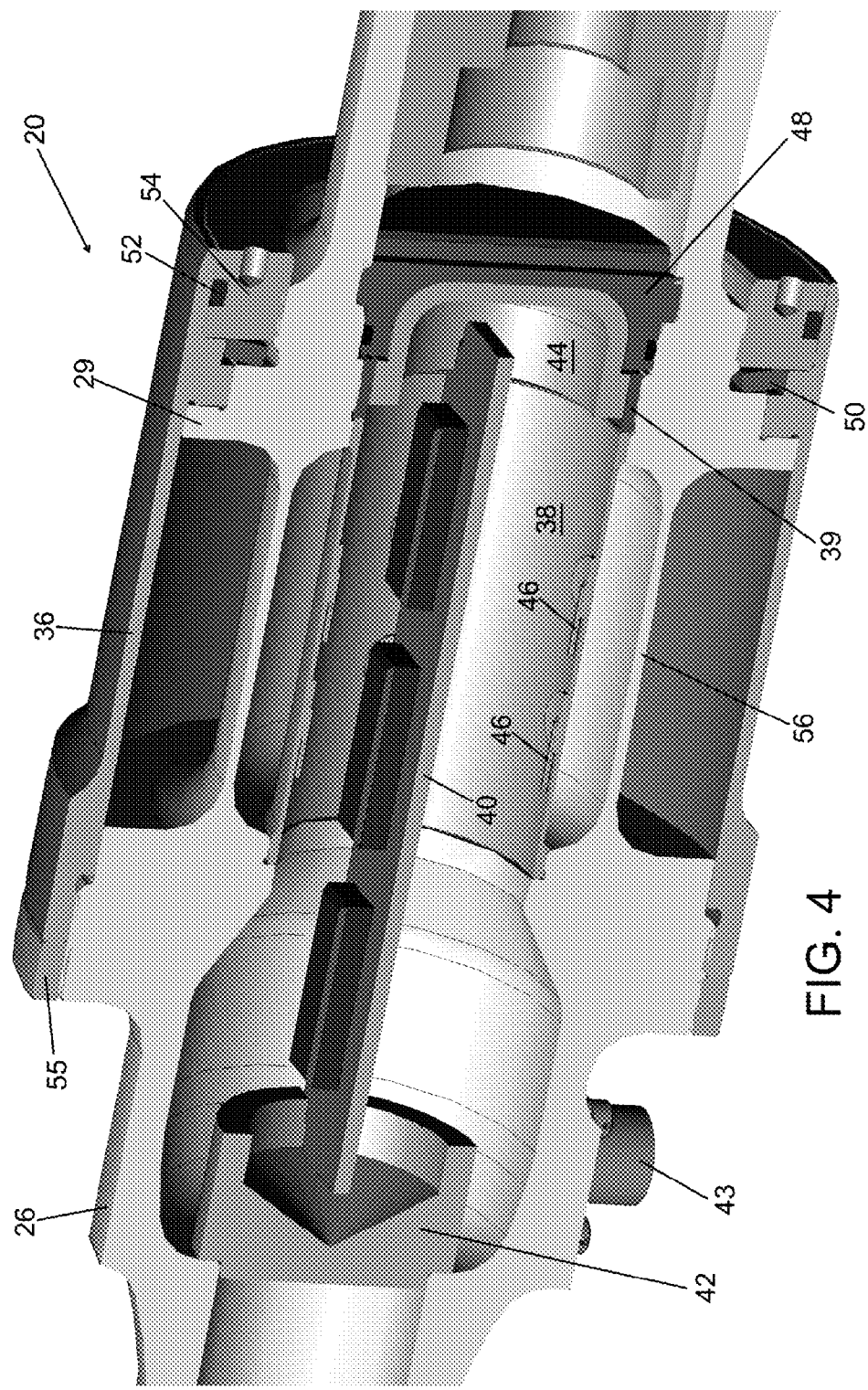
FIG. 4 is an enlarged sectioned perspective view showing a sensing portion of the load sensing drive strut shown in FIG. 2.

FIGS. 2-5 show LSDS 20 in greater detail. In the depicted embodiment, LSDS 20 comprises a main body 26 and a rod end 28 connected to main body 26, wherein LSDS transmits applied loads along a longitudinal axis A of LSDS 20. Spherical bearings 34 are provided at opposite ends 30 and 32 of LSDS 20, however only one spherical bearing 34 is shown in FIG. 3. LSDS 20 further comprises a load alleviation member 36 in the form of an outer tube member surrounding main body 26, and a load sensing member 38 in the form of a sensing sleeve having one end engaged against an internal surface of main body 26 and an opposite end engaged by a threadably adjustable preload nut 39. Load alleviation member 36 is situated between a sealing collar 54 arranged about main body 26 and having an O-ring seal 52 engaging an inner wall of load alleviation member 36, and an abutment ring 55 arranged about main body 26. Load alleviation member 36 includes an internal radial step 37 fitting into an annular space between a flange 29 on main body 26 and sealing collar 54. A Belleville washer 50 maintains a slight gap 58 between radial step 37 and flange 29, and also a slight gap 60 between radial step 37 and sealing collar 54. The purpose of the gaps will be explained in the description below. Gaps 58 and 60 may, for example, be on the order of 0.004 inches (0.1 mm).

LSDS 20 also includes a circuit card 40 which may be arranged to extend axially through load sensing member 38 and held at its opposite ends by circuit card supports 42 and 44, which may be thermoplastic supports. Circuit card 40 may be mounted so as to resist vibratory loads in axial and lateral directions.

In order to measure loading experienced by load sensing member 38, a plurality of strain gauge sensors 46 may be arranged on an internal wall surface of load sensing member 38. Sensors 46 may, for example, be metallic foil or semiconductor/piezoelectric sensors. Leads (not shown) from sensors 46 connect the sensors to circuit board 40, whereby analog signals from sensors 46 may be inputted to circuit board 40. In a current embodiment, a plurality of gauges may be angularly spaced about a central axis of sensor sleeve 38 at a common axial position along the central axis to provide a single measurement channel, and a plurality of measurement channels may be provided at axially spaced locations along load sensing member 38. Such an arrangement is advantageous to allow for cancellation of bending stresses and temperature compensation. It is noted that an ideal strut would experience only axial tensile and compressive stress and strain. However, due to imperfect end attachment bearings, the LSDS 20 may experience bending moments due to bearing friction. Therefore, the total stress/strain state at a given axial position along load sensing member 38 is the superposition of axial compressive or tensile stress and normal stress due to bending. At a neutral bending axis of load sensing member 38, only the axial tensile or compressive components are present. It is desired to only sense the axial component since it is related to the loading of interest. To ensure that this is the case, the strain gauges may be placed on the neutral axis. For example, two gauges on each side spaced axially apart a small distance. The gauges may also be placed above and below the neutral axis. With this arrangement the bending tensile and compressive components cancel leaving only the desired axial strain. By way of non-limiting example, eight sensors 46 may be provided for each measurement channel, and two separate channels may be provided. As may be understood, load sensing member 38 has a uniform cross section area over an axial length sufficient to mount sensors 46 and is reasonably far from abrupt transitions.

After sensors 46 and electronics 40 are installed, an O-ring sealed plug 48 is installed adjacent circuit card support 44 to ensure a hermetic cavity (the opposite end of the cavity is a blind cavity and therefore hermetic). Compliant rubber-like potting may be used where appropriate to ensure leads are not vulnerable to vibratory conditions. Two leads from each measurement channel may be routed from circuit card 40 through holes 41 in a tubular structure 43 and attached to hermetic connectors (not shown), whereby signals from LSDS may be transmitted to a SFCC or other control unit.

Figure 5:
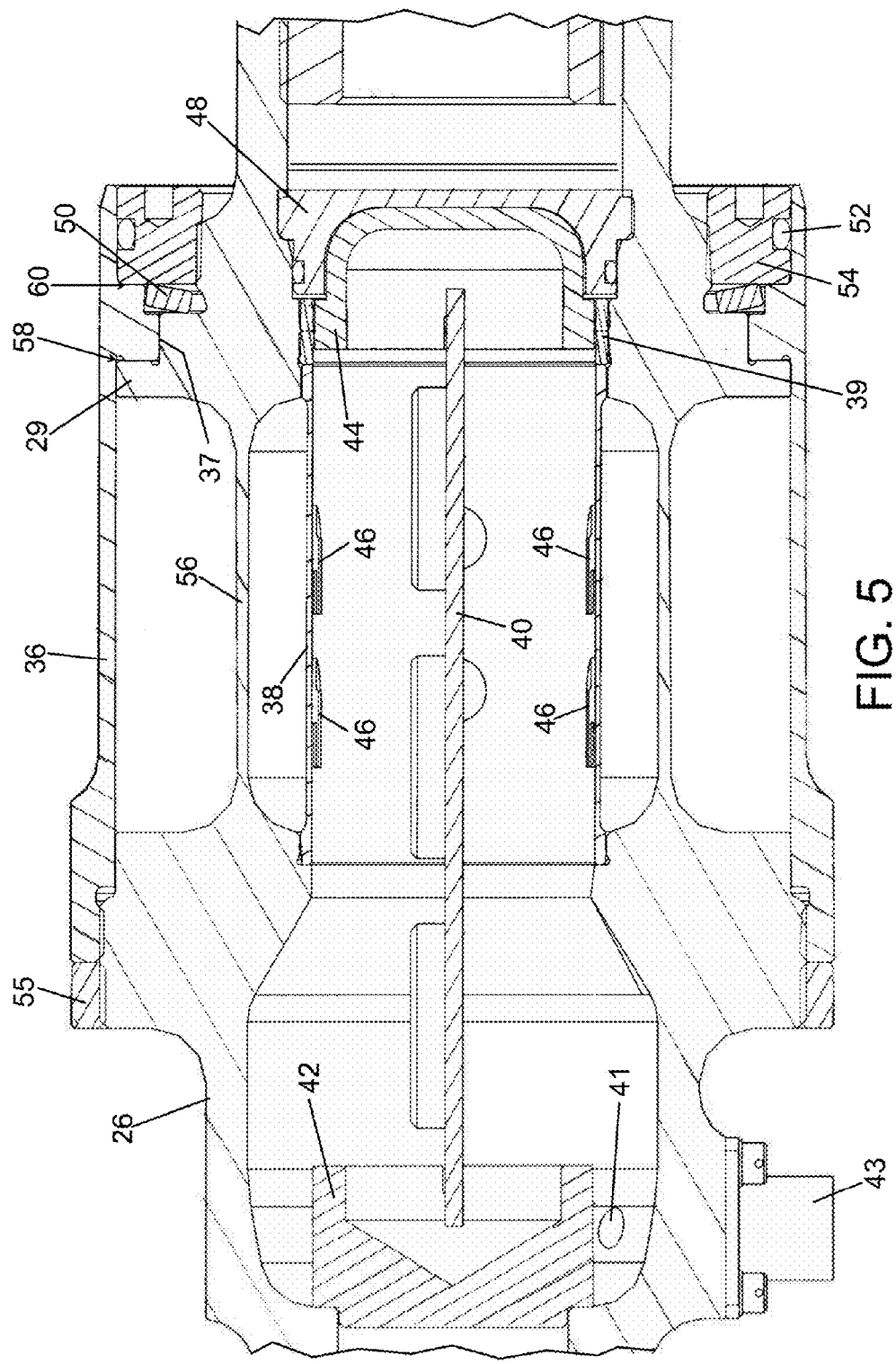
FIG. 5 is a cross-sectional view of the sensing portion shown in FIG. 4.
Figure 6:
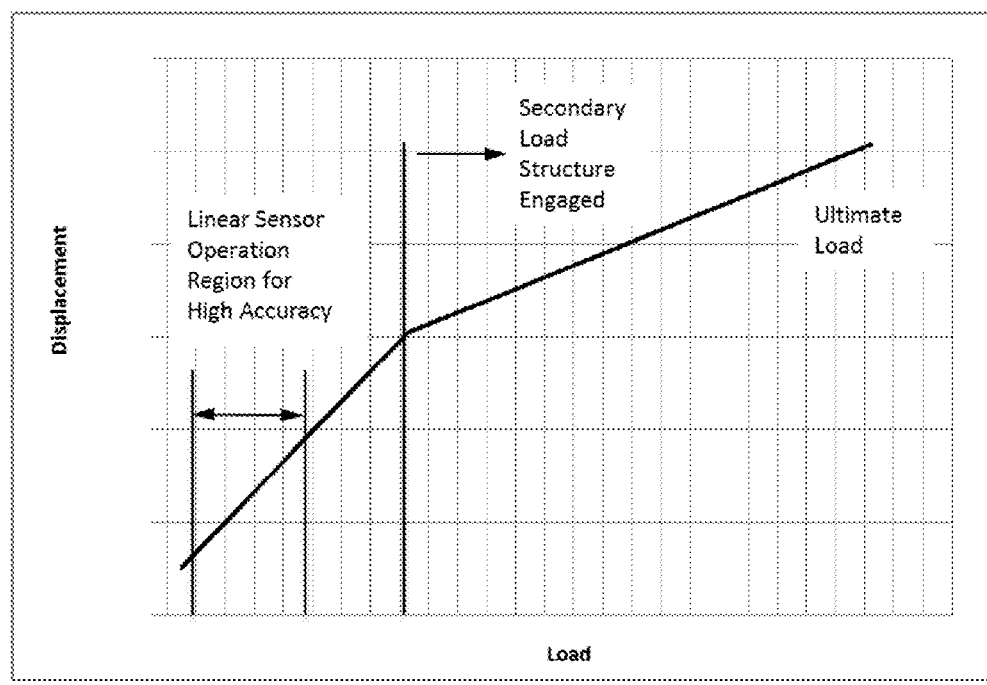
FIG. 6 is a graph of displacement versus load for a load sensing member of the load sensing drive strut, illustrating a non-linear loading scheme of the present invention.

To obtain good sensitivity for relatively low load conditions, special attention was given to load paths through LSDS 20. For low to moderate loads, the load path is through load sensing member 38 and an intermediate wall 56 of main body 26. Load alleviation member 36 is used to react to larger loads. As external loading increases, elastic deformation occurs and the preset gaps 58 and 60 begin to close. After a predetermined load is reached the gap corresponding to tension or compression load becomes fully closed. Increased loads are then shared with load alleviation member 36. Thus, when loading is outside a predetermined range, load alleviation member 36 alleviates load that would otherwise be carried by load sensing member 38 and measured by sensors 46. This loading behavior is illustrated in FIG. 5. As may be seen, when the load level is low, an incremental increase in load results in a relatively large displacement of load sensing member 38 which is measured by sensors 46. Once load alleviation member 36 is engaged, the same incremental increase in load results in a reduced displacement of load sensing member 38. Consequently, the present invention allows higher strain and sensitivity for sensors 46 of LSDS 20 in a low to moderate load range, while also providing high strength capable of reacting to very high loads.

Returning to the example of an aircraft flap system, if there is a disconnect failure of LSDS 20, the load experienced by LSDS will reduce significantly. Accordingly, SFCC may be programmed to halt further drive commands to rotary actuator 16 if the load sensed by LSDS 20 drops below a predetermined threshold value. In this way, the SFCC inhibits further flap movement to prevent damage.

What is claimed is:

1. A load-sensing strut comprising:
a main body having a longitudinal loading axis along which an applied load is transmitted;
a load sensing member arranged to carry at least a portion of the applied load when the applied load is within a predetermined loading range, wherein the load sensing member includes at least one load sensor generating a load signal, wherein the load sensing member includes a cylindrical sleeve aligned on the loading axis; and
a load alleviation member arranged to reduce the portion of the applied load carried by the load sensing member when the applied load is outside the predetermined loading range, wherein the load alleviation member includes an outer tube member surrounding the main body to define first and second longitudinal abutment gaps between the main body and the load alleviation member whereby the load alleviation member is disengaged from transmitting the applied load when the applied load is within the predetermined loading range;
the load alleviation member being engaged to assist the main body and the load sensing member in transmitting the applied load in response to longitudinal deformation of the main body caused by the applied load being outside the predetermined loading range;
wherein the at least one load sensor exhibits greater sensitivity to incremental changes in the applied load when the applied load is within the predetermined loading range than when the applied load is outside the predetermined loading range.

2. The load-sensing strut according to claim 1, wherein the predetermined loading range includes a tension load and a compression load.

3. The load-sensing strut according to claim 1, further comprising a preload member operable to apply an axially-directed preload to the load sensing member.

4. The load-sensing strut according to claim 1, wherein the preload member is a nut threadably adjustable relative to the main body to apply a preload to the load sensing member.

5. The load-sensing strut according to claim 1, wherein the at least one load sensor comprises a first plurality of load sensors applied to a surface of the cylindrical sleeve and angularly spaced about the loading axis at a first axial location.

6. The load-sensing strut according to claim 5, wherein the at least one load sensor further comprises a second plurality of load sensors applied to the surface of the cylindrical sleeve and angularly spaced about the loading axis at a second axial location spaced from the first axial location.

7. The load sensing strut according to claim 1, wherein the load alleviation member is aligned on the loading axis.

8. The load sensing strut according to claim 1, wherein the load alleviation member is situated between a collar arranged about the main body and an abutment ring arranged about the main body.

9. The load sensing strut according to claim 8, wherein main body includes a flange opposing the collar to define an annular space between the flange and the collar, and the load alleviation member includes an internal radial step received in the annular space.

10. The load sensing strut according to claim 9, further comprising an elastically deformable member arranged between the flange and the collar, wherein the elastically deformable member maintains the first gap between the flange and the internal radial step and the second gap between the collar and the internal radial step when the applied load is within the predetermined loading range.

11. The load sensing strut according to claim 10, wherein at least one of the first gap and the second gap closes when the applied load is outside of the predetermined loading range.

12. The load sensing strut according to claim 1, wherein the main body includes an intermediate wall extending along the loading axis radially inward from the load alleviation member, and wherein the applied load is transmitted through the load sensing member and the intermediate wall, and not through the load alleviation member, when the applied load is within the predetermined loading range.

13. The load sensing strut according to claim 12, wherein the applied load is transmitted through the load sensing member, the intermediate wall, and the load alleviation member when the applied load is outside of the predetermined loading range.

* * * * *